United States Patent
Kondo et al.

(10) Patent No.: US 7,628,777 B2
(45) Date of Patent: Dec. 8, 2009

(54) ABSORBENT ARTICLE HAVING PASSAGE HOLES IN A CENTRAL REGION

(75) Inventors: Hideki Kondo, Kagawa (JP); Jun Kudo, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 339 days.

(21) Appl. No.: 10/238,432

(22) Filed: Sep. 9, 2002

(65) Prior Publication Data
US 2003/0050618 A1    Mar. 13, 2003

(30) Foreign Application Priority Data
Sep. 11, 2001   (JP)   .............................. 2001-275814

(51) Int. Cl.
A61F 13/15   (2006.01)
A61F 13/20   (2006.01)

(52) U.S. Cl. .............................. 604/385.101; 604/378; 604/385.01

(58) Field of Classification Search ......... 604/378–383; 428/131–140, 103
See application file for complete search history.

(56) References Cited

U.S. PATENT DOCUMENTS

| | | | | |
|---|---|---|---|---|
| 3,730,184 A | * | 5/1973 | Mesek | 604/365 |
| 4,184,902 A | | 1/1980 | Karami | |
| 4,735,843 A | * | 4/1988 | Noda | 428/137 |
| 4,846,813 A | * | 7/1989 | Raley | 604/385.08 |
| 4,908,026 A | * | 3/1990 | Sukiennik et al. | 604/378 |
| 5,415,640 A | * | 5/1995 | Kirby et al. | 604/383 |
| 5,437,653 A | * | 8/1995 | Gilman et al. | 604/378 |
| 5,533,991 A | | 7/1996 | Kirby et al. | |
| 5,591,149 A | * | 1/1997 | Cree et al. | 604/378 |
| 5,613,962 A | * | 3/1997 | Kenmochi et al. | 604/378 |
| 5,746,729 A | * | 5/1998 | Wada et al. | 604/378 |
| 5,803,920 A | * | 9/1998 | Gilman | 604/378 |
| 5,833,678 A | * | 11/1998 | Ashton et al. | 604/378 |
| 5,855,719 A | * | 1/1999 | Menard | 156/256 |
| 5,919,177 A | * | 7/1999 | Georger et al. | 604/367 |
| 5,954,705 A | * | 9/1999 | Sawaki et al. | 604/385.101 |
| 5,961,505 A | * | 10/1999 | Coe et al. | 604/378 |
| 6,093,871 A | * | 7/2000 | Takai et al. | 604/383 |
| 6,274,218 B1 | * | 8/2001 | Shimizu | 428/137 |
| 6,528,698 B2 | * | 3/2003 | Mizutani et al. | 604/382 |
| 6,932,798 B2 | * | 8/2005 | Kudo et al. | 604/385.01 |

(Continued)

FOREIGN PATENT DOCUMENTS

EP   0 165 807 A1   12/1985

(Continued)

OTHER PUBLICATIONS

Japanese Patent Office Action for Appl. No. 2002-253890, mailing date Nov. 6, 2007.

*Primary Examiner*—Michele Kidwell
(74) *Attorney, Agent, or Firm*—Darby & Darby P.C.

(57) ABSTRACT

An absorbent article is elongated to have longitudinally opposed front and rear edges and transversely opposed left and right edges. The absorbent article includes a stack of: a backsheet having a liquid barrier effect; a liquid absorbent layer; a hydrophilic intermediate sheet including fibers; and a hydrophilic topsheet including fibers. The absorbent article has a central region of a predetermined width, which is spaced apart from the left and right edges and formed with a plurality of liquid passage holes continuously extending from the topsheet to the intermediate sheet.

13 Claims, 5 Drawing Sheets

U.S. PATENT DOCUMENTS

| | | | |
|---|---|---|---|
| 2001/0051795 A1* | 12/2001 | Bissah et al. | 604/333 |
| 2002/0029025 A1* | 3/2002 | Furuya et al. | 604/378 |
| 2003/0149410 A1* | 8/2003 | Kudo et al. | 604/367 |

FOREIGN PATENT DOCUMENTS

| | | |
|---|---|---|
| JP | 60-60405 | 4/1985 |
| JP | 64-020844 | 1/1989 |
| JP | 01-158953 | 6/1989 |
| JP | 08-302568 | 3/1996 |
| JP | 2001-238910 | 9/2001 |
| WO | WO-93/11726 A1 | 6/1993 |
| WO | WO-99/55532 | 11/1999 |
| WO | WO-01/72251 A1 | 10/2001 |

* cited by examiner

ABSORBENT ARTICLE HAVING PASSAGE HOLES IN A CENTRAL REGION

INCORPORATION BY REFERENCE

The present application claims priority under 35 U.S.C. §119 to Japanese Patent Application No. 2001-275814 filed on Sep. 11, 2001, the entire contents of which being hereby incorporated herein by reference.

BACKGROUND OF THE INVENTION

1. Field of the Invention

The present invention relates to a thin absorbent article such as vaginal discharge absorbing sheet called panty liner, urine absorbing sheet for a patient suffering from urinary incontinence, absorbing sheet for receiving a small amount of menstrual blood, or the like.

2. Description of the Related Art

Thin absorbent articles such as panty liner are worn by adhering and fixing onto an inner side of a crotch portion of an undergarment through a pressure sensitive adhesive.

Figure 6:
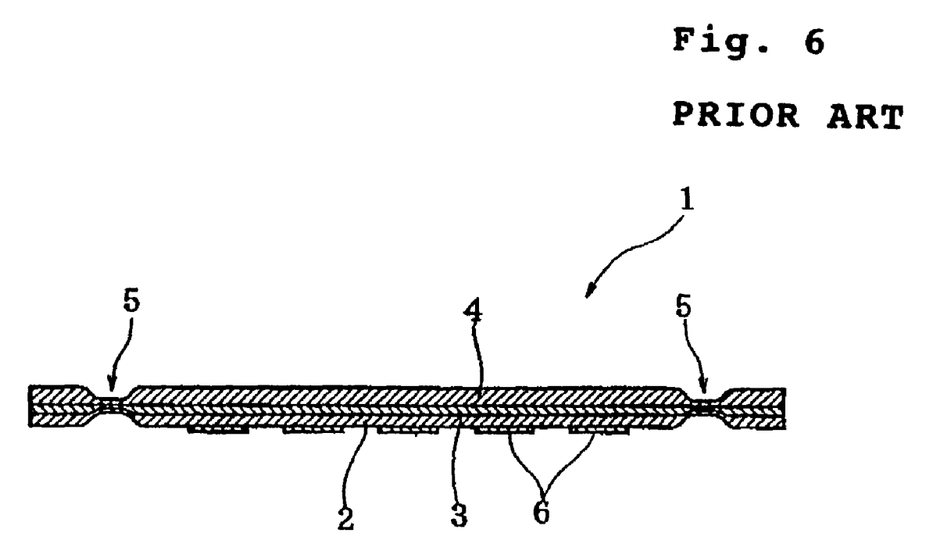
FIG. 6 is a sectional view of a conventional absorbent article.

FIG. 6 is a sectional view showing a conventional, commonly used thin absorbent article 1.

In the absorbent article 1, a single- or two-layer intermediate layer 3 is disposed on a backsheet 2 formed of synthetic resin film and having a liquid barrier effect, and a topsheet 4 formed of hydrophilic nonwoven fabric is laid thereon. Along the periphery of the absorbent article 1, there is formed a round-sealed portion 5 where the backsheet 2, intermediate layer 3 and topsheet 4 are thermal bonded. On the garment surface of the backsheet 2, on the other hand, there is provided a pressure sensitive adhesive layer 6 for adhering and fixing to an inner side of a crotch portion of an undergarment.

When the thin absorbent article 1 is adapted for use as panty liner or the like, the topsheet 4 is formed of spunlaced nonwoven fabric comprising hydrophilic fibers such as rayon, and the intermediate layer 3 is formed of a bundle of hydrophobic fibers or water-repellent nonwoven fabric. The absorbent article 1 of this kind aims at receiving a minute amount of body waste or discharged liquid such as vaginal discharge, and is made extremely thin so as to feel integrated with the crotch portion of the undergarment. To this end, the body waste or discharged liquid is absorbed mainly by the hydrophilic topsheet 4, but the intermediate layer 3, which is hydrophobic or water-repellent having no liquid absorbing function, functions as a cushion layer for improving contact feel with the skin of a wearer.

The thin absorbent article 1 of this kind is, for instance, used for locally absorbing and retaining a vaginal discharge or the like discharged from a vaginal opening of a female. In this case, the vaginal discharge or the like is given to the central region of the absorbent article 1 in a concentrated manner and absorbed and retained by the topsheet 4. However, since the conventional absorbent article absorbs the liquid only with the thin topsheet 4, when worn for a long time, the locally applied liquid is easily saturated and left on the surface of the topsheet 4 to give an unpleasant feel to a wearer. As vaginal discharge absorbing sheets, moreover, there has been known a long-size type having an entire length of equal to or larger than 160 mm. However, since it can absorb the liquid only locally with the topsheet 4, the long topsheet 4 can not be effectively utilized, so that the locally applied liquid is liable to provide an unpleasant feel.

In addition since the liquid is absorbed only with the topsheet 4 in the prior art, the liquid absorption speed is low. Therefore, if it is, for instance, used as a pad for a patient suffering from mild urinary incontinence and a relatively large amount of liquid is given thereto, such liquid cannot be absorbed in a short period of time, readily causing lateral liquid leakage from the absorbent article 1.

Of course, if a thick absorbent layer mainly comprising pulp or the like is provided between the backsheet and the topsheet as in sanitary napkins and disposable diapers, the liquid absorption capacity can be increased. However, the absorbent article 1 of this kind must be thin so as to feel integrated with a crotch portion of an undergarment upon wearing, and its thickness is required to be equal to or smaller than 3 mm, preferably equal to or smaller than 2 mm, for instance. Accordingly, it is impossible to provide such thick absorbent layer.

It is also conceivable to provide an extremely thin absorbent layer such as a stack of tissue paper or airlaid pulp between the backsheet and the topsheet. However, since the vaginal discharge or the like is locally given to the topsheet in a concentrated manner, it is impossible to increase the absorption capacity of the locally applied liquid only by providing such thin absorbent layer, so that it is impossible to wear it for a long time.

SUMMARY OF THE INVENTION

The present invention has been worked out in view of the shortcoming in the prior art set forth above. It is therefore an object of the present invention to provide a thin absorbent article in which a minute amount of liquid locally applied in a concentrated manner can be rapidly diffused over a large area for absorption and retention to substantially increase an absorption capacity of the liquid, thereby making it possible to wear the absorbent article for a long time.

According to the present invention, there is provided an absorbent article elongated to have longitudinally opposed front and rear edges and transversely opposed left and right edges, the absorbent article comprising a stack of:
 a backsheet having a liquid barrier effect;
 a liquid absorbent layer;
 a hydrophilic intermediate sheet including fibers; and
 a hydrophilic topsheet including fibers,
 wherein the absorbent article has a central region of a predetermined width, which is spaced apart from the left and right edges and formed with a plurality of liquid passage holes continuously extending from the topsheet to the intermediate sheet.

In the absorbent article of the present invention, the topsheet, the intermediate sheet underlying the topsheet, and the liquid absorbent layer underlying the intermediate sheet are all hydrophilic. A discharged liquid such as vaginal discharge locally given to the central region is attracted into the inside of the absorbent article due to capillary action of the plurality of liquid passage holes continuously extending from the topsheet to the intermediate sheet in the central region, diffused to surroundings through the intermediate sheet, and then absorbed by the liquid absorbent layer underlying the intermediate sheet. Accordingly, even if the liquid absorbent layer, intermediate sheet and topsheet are made thin to provide a thin structure as a whole, the locally given liquid can be absorbed while being diffused. Therefore, the absorbent article of the present invention can be made thin and used for a long time.

For example, the central region extends longitudinally of the absorbent article in a strip shape of a predetermined width and the liquid passage holes are uniformly distributed in the central region. In the case where the liquid passage holes are longitudinally distributed, the discharged liquid can be absorbed while being longitudinally diffused on the surface of the absorbent article due to capillary action of the liquid passage holes. Accordingly, the absorption capacity of the elongated absorbent article can be widely used along its longitudinal direction.

Preferably, a fiber density of the intermediate sheet is higher than a fiber density of the topsheet in the central region. By making the fiber density of the intermediate sheet higher in the central region, the liquid passing through the liquid passage holes can be positively diffused through the intermediate sheet. In order to exhibit such diffusing function effectively, a difference in fiber density between the topsheet and the intermediate sheet in the central region is preferably equal to or higher than 0.01 g/cm$^3$. It should be noted that the fiber densities in the central region means fiber densities of portions having no liquid passage hole formed therein (e.g., portions between adjacent liquid passage holes).

Preferably, at least one of the topsheet and the intermediate sheet is formed of through-air bonded nonwoven fabric, of which synthetic fibers are thermal bonded to each other with hot air. If through-air bonded nonwoven fabric is used, a soft contact feel can be provided to the skin of a wearer during wear. In addition, since the distance between adjacent fibers is relatively large in through-air bonded nonwoven fabric, the synthetic fibers are hardly cut at the holes during formation of the liquid passage holes, so that the shape of the holes can be maintained.

It is also possible that fibers forming the topsheet are coated with an initial hydrophilic agent and fibers forming the intermediate sheet are coated with a durable hydrophilic agent. In the case where the fibers forming the intermediate sheet is coated with the durable hydrophilic agent, hydrophilicity of the intermediate sheet can be maintained for a long time, so that the liquid diffused in the intermediate sheet can permeate the liquid absorbent layer for a long time. In this case, it is preferred that the intermediate sheet includes a bottom layer adjacent to the liquid absorbent layer and a top layer adjacent to the topsheet, and fibers forming the bottom layer are coated with the durable hydrophilic agent and fibers forming the top layer are coated with the initial hydrophilic agent. In the case where the fibers forming the bottom layer of the intermediate sheet are coated with the durable hydrophilic agent, the bottom layer of the intermediate sheet can remain hydrophilic for a long time, so that the liquid diffused in the intermediate sheet can be readily given to the liquid absorbent layer. That is, it is preferred that hydrophilicity of the bottom layer of the intermediate sheet is higher than hydrophilicity of the top layer of the intermediate sheet, and hydrophilicity of the topsheet is equal to or higher than the hydrophilicity of the bottom layer of the intermediate sheet. With the hydrophilicities being set as above, the liquid given to the topsheet passes through the top layer of the intermediate sheet while being attracted to the bottom layer, and thereafter, it readily permeates the liquid absorbent layer. Accordingly, the locally given liquid can be readily diffused and absorbed.

Preferably, the topsheet and the intermediate sheet are bonded through an adhesive layer which is applied in a plurality of strips extending longitudinally of the absorbent article and spaced apart from each other transversely of the absorbent article. In the case where the adhesive layer is applied in such plurality of strips extending longitudinally of the absorbent article, the adhesive layer can exhibit a function of diffusing the liquid longitudinally of the absorbent article. In this case, if the adhesive layer is provided in regions transversely outside the central region having the liquid passage holes formed therein, the adhesive layer does not prevent permeation of the liquid through the liquid passage holes. In addition, since the surface for contacting the skin of a wearer is not stiffened in the central region, it feels comfortable to wear and hardly has a bad influence upon the skin.

Preferably, the intermediate sheet and the liquid absorbent layer are likewise bonded through an adhesive layer which is applied in a plurality of strips extending longitudinally of the absorbent article and spaced apart from each other transversely of the absorbent article.

Preferably, each liquid passage hole is elongated longitudinally of the absorbent article to have a longitudinal dimension larger than a transverse dimension, and the longitudinal dimension of each liquid passage hole is gradually decreased as extending from a body surface of the topsheet to the intermediate sheet. In the case where the liquid passage holes are elongated longitudinally of the absorbent article, the discharged liquid passing through the liquid passage holes can be given to the intermediate sheet while being diffused longitudinally of the absorbent article.

The absorbent article of the present invention has a thickness preferably equal to or smaller than 3 mm, more preferably equal to or smaller than 2 mm, most preferably equal to or smaller than 1.5 mm, so that when it is adhered and fixed on an inner side of a crotch portion of an undergarment, it can feel integrated with the undergarment during wear.

The present invention will be more effective if the absorbent article is constructed as a so-called long-size type having an entire length equal to or larger than 160 mm. In the present invention, the liquid given to the topsheet can be absorbed while being diffused in the central region longitudinally of the absorbent article, and then, likewise diffused through the intermediate sheet longitudinally of the absorbent article for absorption by the liquid absorbent layer. Therefore, if the absorbent article is of the long-size type, its length can be effectively utilized.

The absorbent article of the present invention is suitable for use as a vaginal discharge absorbing sheet.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
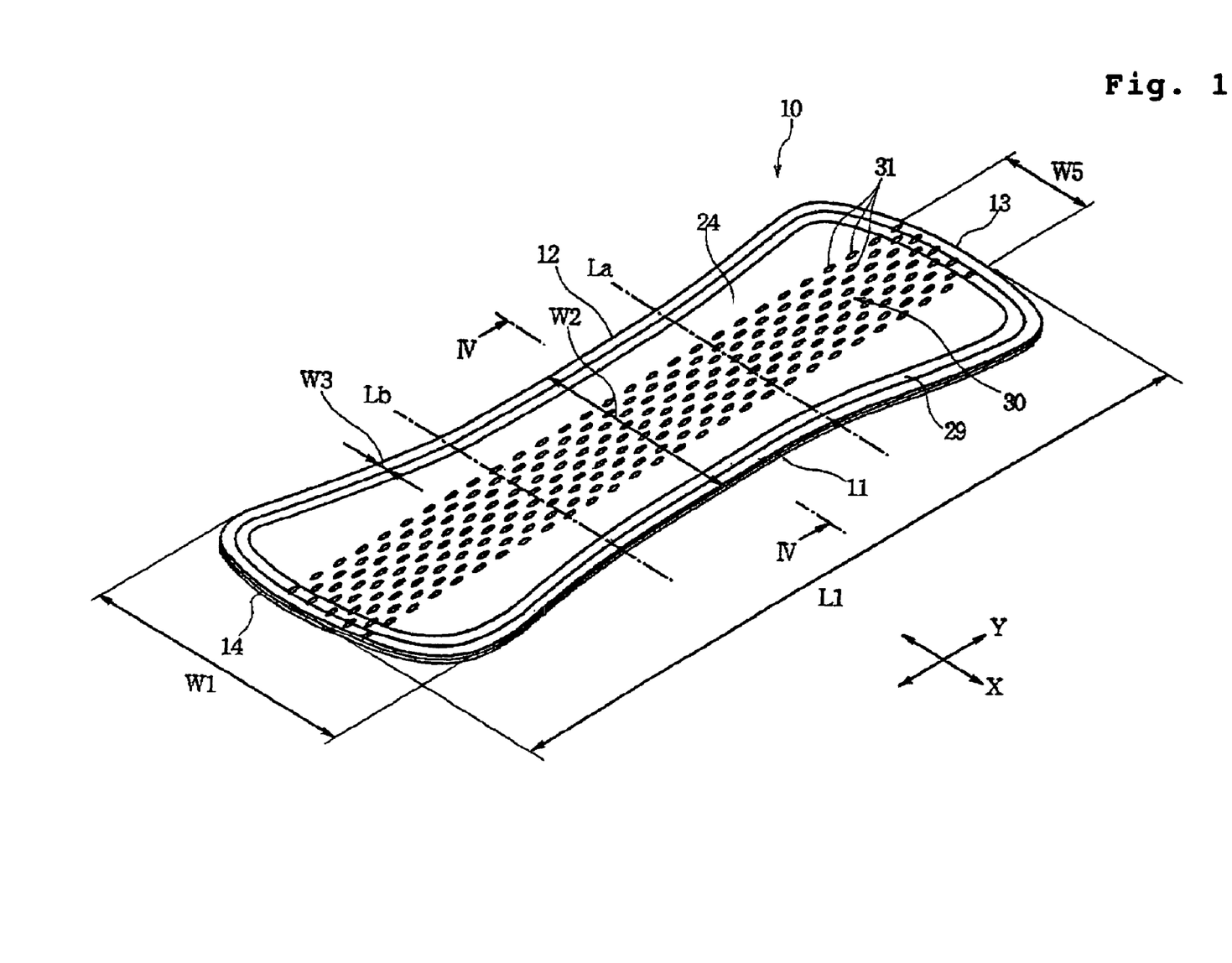
FIG. 1 is a perspective view showing an absorbent article according to one embodiment of the present invention.
Figure 2:
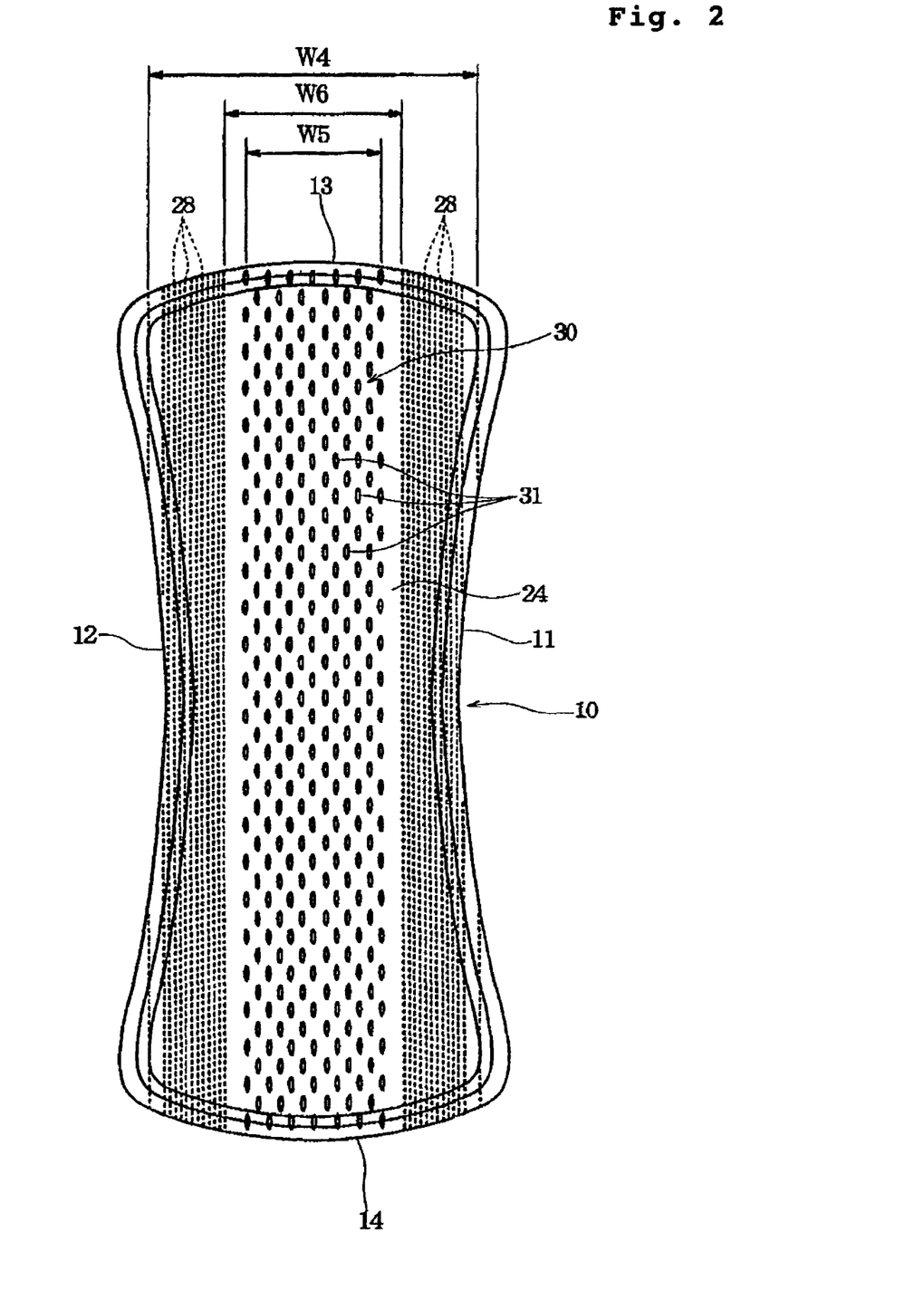
FIG. 2 is a top plan view of the absorbent article.
Figure 3:
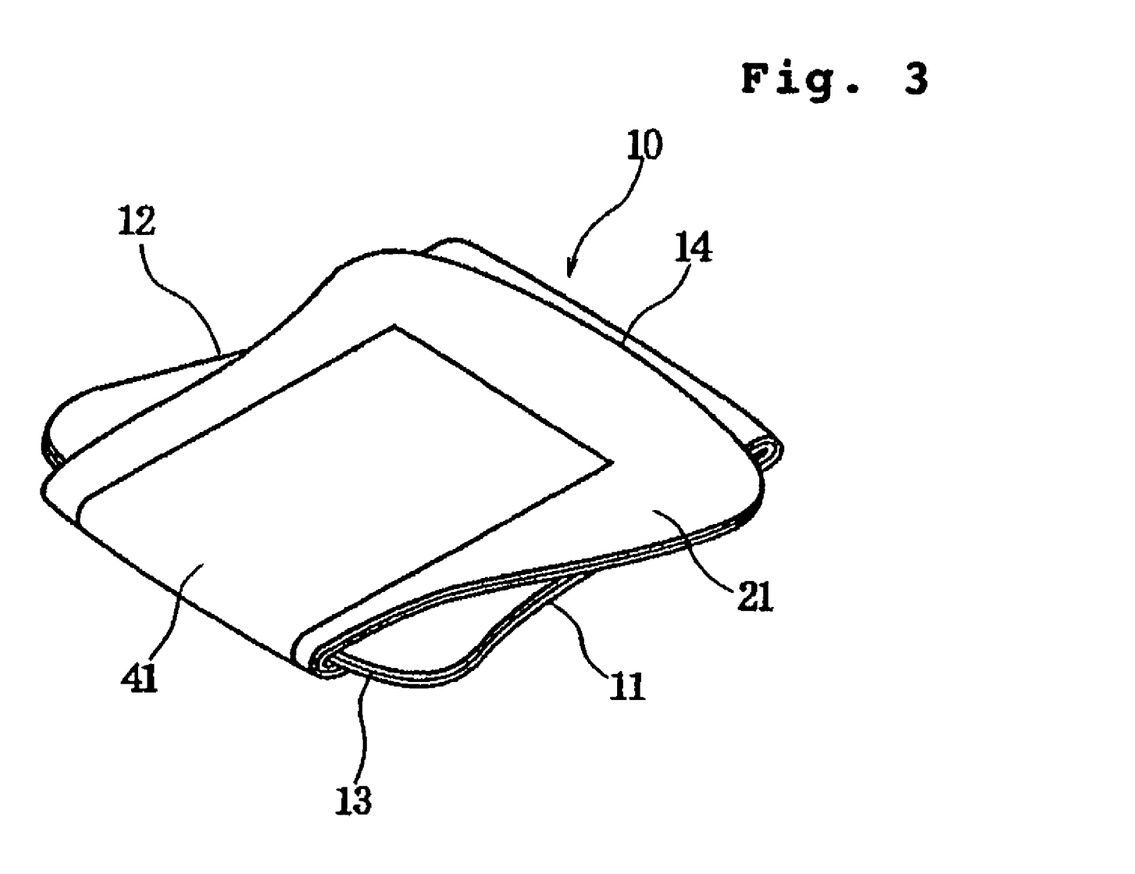
FIG. 3 is a perspective view showing a state where the absorbent article is folded.
Figure 4:
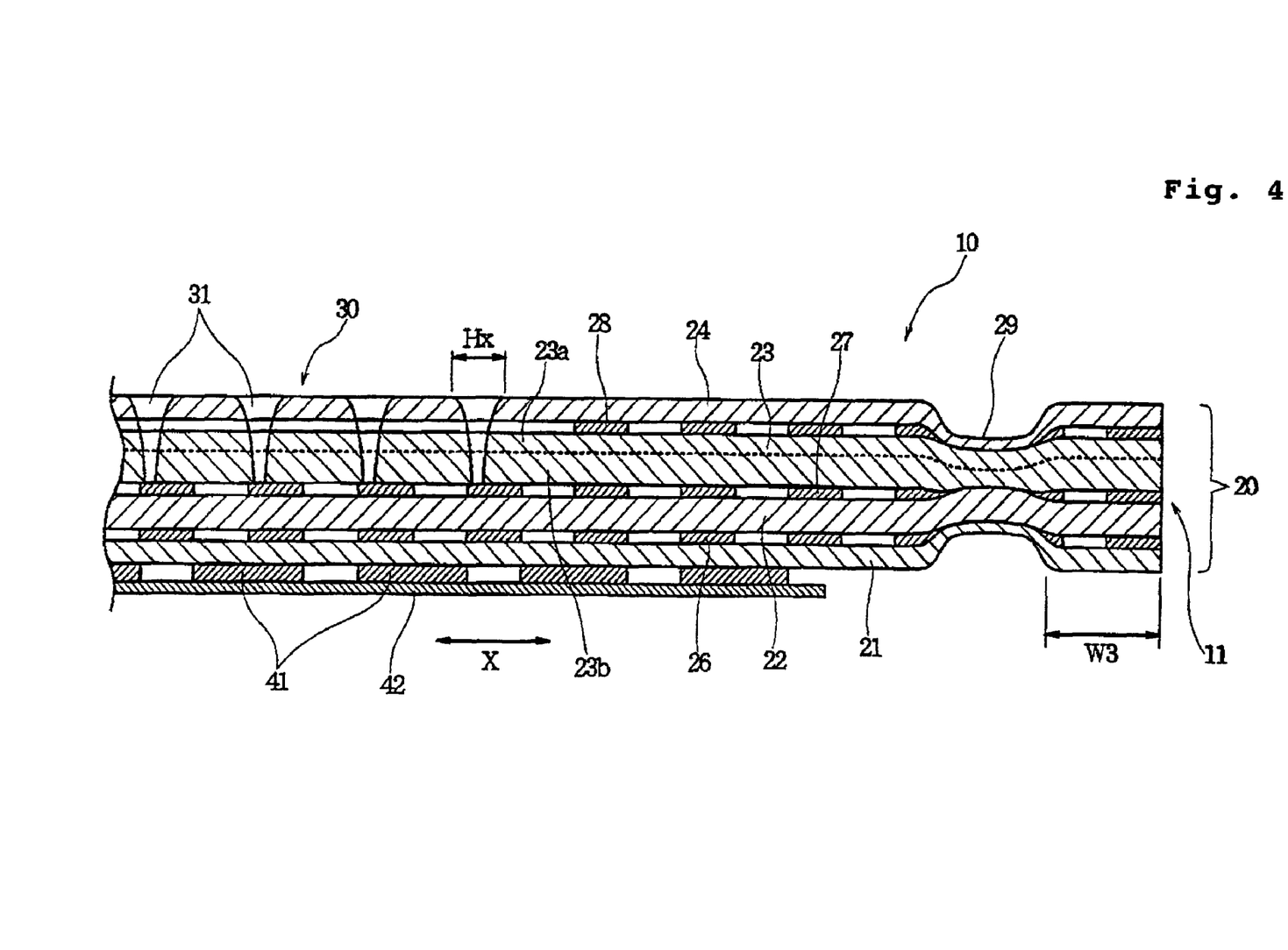
FIG. 4 is a partially sectional view taken along line IV-IV of FIG. 1.
Figure 5:
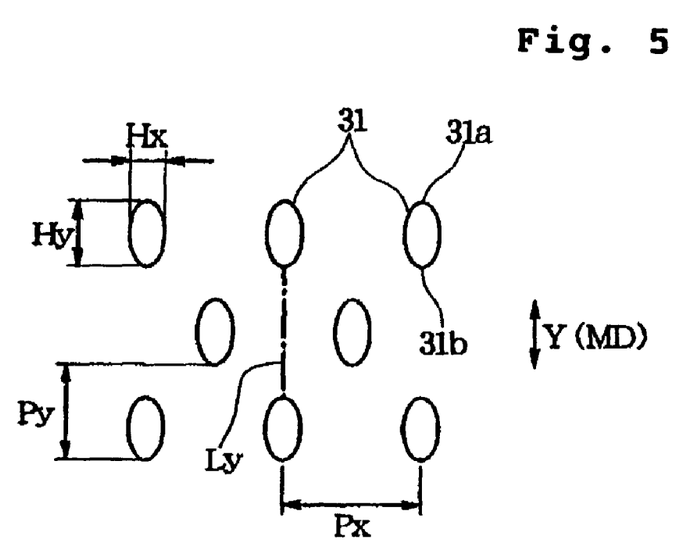
FIG. 5 is an enlarged top plan view showing liquid passage holes.

FIG. 1 is a perspective view showing a vaginal discharge absorbing sheet (panty liner) 10 (hereinafter called merely "absorbing sheet 10") in a developed state, as a thin absorbent article according to one embodiment of the present invention; FIG. 2 is a top plan view of the absorbing sheet 10; FIG. 3 is a perspective view showing a state where the absorbing sheet 10 is folded in three; FIG. 4 is a partially sectional view showing part of a section taken along line IV-IV of FIG. 1; and FIG. 5 is an enlarged top plan view showing a pattern of liquid passage holes.

The vaginal discharge absorbing sheet 10 refers to a thin absorbent article, which is to be worn by a female while being fixed on an inner side of a crotch portion of an undergarment and integrated with the undergarment, aiming to absorb a liquid discharged from a female, such as vaginal discharge. However, the thin absorbent article of the present invention should not be limited thereto, but may also be worn by a female while being fixed on an inner side of a crotch portion of an undergarment to absorb a minute amount of urine upon urinary incontinence or a small amount of menstrual blood.

In the shown embodiment, the absorbing sheet 10 has right and left edges 11 and 12 extending in a longitudinal direction (Y-direction) and front and rear edges 13 and 14 extending in a transverse direction (X-direction). The front and rear edges 13 and 14 are outwardly curved. The right and left edges 11 and 12 are inwardly curved, so that the absorbing sheet 10 is of an hourglass shape in top plan view. The absorbing sheet 10 is of a so-called long-size type having a length (longitudinal dimension) L1 of 160 to 210 mm, preferably 165 to 200 mm, more preferably 170 to 190 mm. A maximum width (transverse dimension) W1 is 60 to 80 mm and a minimum width W2 is 30 to 65 mm. More preferably, W2 is about 45 to 65 mm. In addition, the absorbing sheet 10 is of a thin type having a thickness of at most 3 mm, preferably at most 2 mm, more preferably at most 1.5 mm. On the other hand, the lower limit of the thickness is about 0.6 mm.

As shown in the sectional view of FIG. 4, the absorbing sheet 10 has a main body portion 20, which is a stack of four-layer structure comprising: a backsheet 21; a thin, liquid absorbent layer 22 disposed on the backsheet 21; an intermediate sheet 23 disposed on the liquid absorbent layer 22; and a topsheet 24 disposed on the intermediate sheet 23. It should be noted that individual components of the absorbing sheet 10 have a body surface and a garment surface. As used herein, "body surface" means that surface of the components which is intended to be worn toward or adjacent to the body of the wearer, while the "garment surface" is on the opposite side and is intended to be worn toward or placed adjacent to the undergarment when the absorbing sheet 10 is worn.

The backsheet 21 and the liquid absorbent layer 22 are bonded through a hydrophobic hot-melt adhesive layer 26. The absorbent layer 22 and the intermediate sheet 23 are bonded through a hydrophobic hot-melt adhesive layer 27. The intermediate sheet 23 and the topsheet 24 are bonded through a hydrophobic hot-melt adhesive layer 28.

As shown in FIGS. 2 and 4, the adhesive layer 28, through which the topsheet 24 and the intermediate sheet 23 are bonded, is provided in left and right side regions to leave a region of a width W6 therebetween, in which the adhesive layer 28 is not provided. In each side region, the adhesive layer 28 is applied in a plurality of narrow strips extending in the longitudinal direction of the absorbing sheet 10. In each side region, moreover, these strips of the adhesive layer 28 are arranged at a constant pitch in the transverse direction of the absorbing sheet 10. The adhesive layer 27, through which the intermediate sheet 23 and the liquid absorbent layer 22 are bonded, and the adhesive layer 26, through which the liquid absorbent layer 22 and the backsheet 21 are bonded, are both applied in a plurality of narrow strips extending in the longitudinal direction of the absorbing sheet 10. These strips of the adhesive layers 27 and 26 are arranged at a constant pitch in the transverse direction of the absorbing sheet 10, substantially over the entire width of the absorbing sheet 10.

The main body portion 20, in which the backsheet 21, liquid absorbent layer 22, intermediate sheet 23 and topsheet 24 are stacked, has a round-sealed portion 29 continuously extending along the periphery of the main body portion 20 but inwardly spaced apart from the respective right edge 11, left edge 12, front edge 13 and rear edge 14 by W3=1 to 4 mm. This round-sealed portion 29 has a width of about 1 to 3 mm, in which the individual components of the main body portion 20 are heated under pressure for heat sealing. Between the right edge 11, left edge 12, front edge 13 and rear edge 14 and the round-seal portion 29, there is left a non-sealed region of a width W3, thereby preventing the right edge 11, left edge 12, front edge 13 and rear edge 14 from being stiffened. Therefore, the individual edges hardly cause a foreign body sensation even when they come into contact with the wearer's skin.

The backsheet 21, liquid absorbent layer 22 and topsheet 24 are trimmed into the same size and shape, but the intermediate sheet 23 has a width W4 which is approximately constant as shown in FIG. 2. The width W4 is smaller than the maximum width W1 of the absorbing sheet 10. However, the width W4 is slightly larger than the minimum width W2 of the absorbing sheet 10, so that transversely opposed edges of the intermediate sheet 23 are trimmed into inwardly curved shape along the right and left edges 11 and 12, near the center of the individual edges 11 and 12.

In the region of the width W6 having no adhesive layer 28 provided therein, as shown in FIG. 2, there is provided a central region 30 of a width W5. In the central region 30, liquid passage holes 31 are uniformly distributed. As used herein, "liquid passage hole" means a hole which is formed by applying a mechanical force to a laminate of the topsheet and the intermediate sheet and through which a liquid given to the topsheet can pass. In the shown embodiment, the central region 30 is a strip-shaped region having a constant width W5 and extending over the entire length of the absorbing sheet 10.

In the shown embodiment, both the topsheet 24 and the intermediate sheet 23 are formed of through-air bonded nonwoven fabric, and the liquid passage holes 31 extend continuously from the topsheet 24 to the intermediate sheet 23, as shown in FIG. 4. More specifically, the individual liquid passage holes 31 pass through both the topsheet 24 and the intermediate sheet 23 to provide an upper opening appearing on the body surface of the topsheet 24 and a lower opening facing the liquid absorbent layer 22. However, it is also possible that the individual liquid passage holes 31 passing through the topsheet 24 do not reach to the garment surface of the intermediate sheet 23 but to a position midway between the garment surface and the body surface of the intermediate sheet 23.

In the central region 30, the liquid passage holes 31 are regularly arranged. As shown in FIG. 5, moreover, the individual liquid passage holes 31 are of an elongated shape (elliptical shape) having its major axis directed in the longitudinal direction (Y-direction: MD) of the absorbing sheet 10. The liquid passage holes 31 are arranged at a pitch Py of 4 to 10 mm in the longitudinal direction and at a pitch Px of 2 to 5 mm in the transverse direction. The upper opening of the individual liquid passage hole 31 on the body surface of the topsheet 24 has a longitudinal dimension Hy of 1.5 to 4 mm and a transverse dimension Hx of 0.5 to 1.5 mm. The open area ratio of the liquid passage holes 31 in the central region 30 is in a range of 8 to 20%.

The width W5 of the central region 30, in which the liquid passage holes 31 are uniformly distributed, is preferably in a range of 17 to 30 mm. Within such range, when the absorbing sheet 10 is worn, the central region 30 can face the vaginal opening of the wearer, so that a discharged liquid such as vaginal discharge can be certainly received by the central region 30.

As shown in FIG. 4, the transverse dimension of the individual liquid passage hole 31 is gradually decreased toward the liquid absorbent layer 22. Similarly, the longitudinal dimension of the individual liquid passage hole 31 is gradually decreased toward the liquid absorbent layer 22.

The liquid passage holes 31 thus elongated in the longitudinal direction may be formed through the following processes. At first, the through-air bonded nonwoven fabric for forming the topsheet 24 and the through-air bonded nonwoven fabric for forming the intermediate sheet 23 are bonded through the adhesive layer 28. Then, heated pins are driven through the laminate from the topsheet 24 to the intermediate sheet 23. The pins as used herein have a circular cross-section to form circular holes passing through two sheets of nonwoven fabric. Thereafter, in the process for manufacturing the absorbing sheet 10, the two sheets of nonwoven fabric are stretched in the longitudinal direction (Y-direction) and laid on the liquid absorbent layer 22. By stretching the two sheets of nonwoven fabric in the longitudinal direction, the liquid passage holes 31 elongated in the longitudinal direction can be obtained.

When the nonwoven fabric is stretched in the longitudinal direction, fibers are gathered at imaginary lines Ly (see FIG. 5) longitudinally extending between adjacent liquid passage holes 31, so that the fiber density is increased at front and rear edges 31a and 31b of the individual liquid passage hole 31.

In the shown embodiment, as mentioned above, both the topsheet 24 and the intermediate sheet 23 are formed of through-air bonded nonwoven fabric. Therefore, the absorbing sheet 10 has a pleasant contact feel. In addition, since the distance between adjacent fibers is relatively large in through-air bonded nonwoven fabric, the fibers are hardly cut during formation of the liquid passage holes using the above-mentioned pins or the like, so that the liquid passage holes 31 can be easily formed. Moreover, since synthetic fibers forming through-air bonded nonwoven fabric are relatively stiff, the shape of the liquid passage holes 31 after formation can be maintained for a long time.

It should be noted that the liquid passage holes 31 can be easily formed as long as either one of the topsheet 24 and the intermediate sheet 23 is formed of through-air bonded nonwoven fabric. In order to provide a soft contact feel to the skin and maintain the shape of the upper opening of the liquid passage hole 31 appearing on the body surface of the topsheet 24 for a long time, however, it is preferred that at least the topsheet 24 is formed of through-air bonded nonwoven fabric. Most preferably, both the topsheet 24 and the intermediate sheet 23 are formed of through-air bonded nonwoven fabric, as mentioned above. In the case where only one of the topsheet 24 and the intermediate sheet 23 is formed of through-air bonded nonwoven fabric, the other may be formed of spunlaced nonwoven fabric, point-bonded nonwoven fabric, spunbonded nonwoven fabric or the like.

In the absorbing sheet 10, as mentioned above, the liquid passage holes 31 are uniformly arranged in the central region 30 of the width W5. When a discharged liquid from a vaginal opening is locally given to the body surface of the absorbing sheet 10, at the central region thereof, the liquid passes through the liquid passage holes 31 for permeation. On the body surface of the topsheet 24, therefore, the liquid is hardly diffused toward the left and right side regions outside the central region 30, but absorbed while being diffused in the longitudinal direction along the central region 30 having the liquid passage holes 31 distributed therein. Moreover, since the individual liquid passage holes 31 are elongated in the longitudinal direction and the fiber density is increased in the front and rear edges 31a and 31b of the individual liquid passage holes 31, the discharged liquid passes through the liquid passage holes 31 while being directed to the longitudinal direction.

In the shown embodiment, the through-air bonded nonwoven fabric forming the topsheet 24 comprises 100% of sheath/core type bicomponent synthetic fibers, of which the core is polyethylene terephthalate (PET) and the sheath is polyethylene (PE), and is formed by thermal bonding the bicomponent synthetic fibers using hot air. The bicomponent synthetic fibers forming the topsheet 24, for instance, have a fineness of 2.2 dtex and a fiber length of 44 mm and are coated with a hydrophilic agent for providing fibers with initial hydrophilic property. Throughout this disclosure, such a hydrophilic agent for providing fibers with initial hydrophilic property is referred to as "initial hydrophilic agent." Examples of the initial hydrophilic agent include: an alkyl phosphate ester salt; and an alkyl phosphate metal salt. The basis weight of the topsheet 24 is about 25 g/m$^2$. The density of the topsheet 24 is from 0.03 to 0.09 g/cm$^3$, preferably 0.06 g/cm$^3$. The thickness of the topsheet 24 is equal to or less than 0.5 mm, and the lower limit of the thickness is about 0.2 mm.

On the other hand, the through-air bonded nonwoven fabric forming the intermediate sheet 23 has a two-layer structure, of which one layer facing the topsheet 24 is referred to as top layer 23a and the other layer facing the liquid absorbent layer 22 is referred to as bottom layer 23b. The boundary between the top layer 23a and the bottom layer 23b is indicated by the imaginary dotted line, as shown in FIG. 4. The top layer 23a and the bottom layer 23b are formed of different fibers. Fibers forming the top layer 23a are bicomponent synthetic fibers, of which the core is polypropylene (PP) and the sheath is PE, and, for instance, have a fineness of 3.3 dtex and a fiber length of 44 mm. Fibers forming the bottom layer 23b are bicomponent synthetic fibers, of which the core is PET and the sheath is PE, and, for instance, have a fineness of 2.2 dtex and a fiber length of 51 mm.

Here, a pigment or lubricant may be added to the fibers forming the top sheet 24 and/or the fibers forming the intermediate sheet 23. It is also possible that a whitening filler such as titanium dioxide be added to the fibers forming the topsheet 24 and/or the fibers forming the intermediate sheet 23, preferably to the cores of the sheath/core structure bicomponent synthetic fibers forming the topsheet 24, in an amount of about 2% by weight based on the fiber weight. By whitening the sheet or coloring the sheet with the pigment, the color of the discharged liquid absorbed by the absorbing sheet can be made less recognizable.

The basis weight of the intermediate sheet 23 is 25 g/m$^2$, and the mean fiber density of the entire sheet is from 0.05 to 0.11 g/cm$^3$. The fiber density of the intermediate sheet 23 is higher than that of the topsheet 24, and the difference in fiber density between the intermediate sheet 23 and the topsheet 24 is preferably equal to or higher than 0.01 g/cm$^3$. It is also possible to provide a difference in fiber density between the top layer 23a and the bottom layer 23b in the intermediate sheet 23.

In case where the fiber density of the intermediate sheet 23 is higher than that of the topsheet 24, a liquid given to the topsheet 24 can be readily attracted to the intermediate sheet 23 through the liquid passage holes 31 and readily diffused to surroundings in the intermediate sheet 23.

In case where the fiber density of the bottom layer 23b is higher than that of the top layer 23a in the intermediate sheet 23, on the other hand, the liquid diffused in the intermediate sheet 23 can be widely diffused toward the garment surface facing the liquid absorbent layer 22, so that the liquid can permeate the liquid absorbent layer 22 in the diffused area.

It should be noted that the fiber densities of the topsheet 24 and the intermediate sheet 23 means fiber densities of portions having no liquid passage hole 31 in the central region 30.

In the intermediate sheet 23, moreover, the bicomponent synthetic fibers forming the top layer 23a are coated with an initial hydrophilic agent, and the bicomponent synthetic fibers forming the bottom layer 23b are coated with a hydrophilic agent for providing fibers with durable hydrophilic property. Throughout this disclosure, such a hydrophilic agent for providing fibers with durable hydrophilic property is referred to as "durable hydrophilic agent." Examples of the durable hydrophilic agent include: a mixture of an alkyl phosphate ester salt containing 10 to 30 carbon atoms and one compound selected from a betaine compound containing 10 to 30 carbon atoms, a sulfuric ester salt and a sulfonate salt; and a mixture of an alkyl phosphate ester salt and a polyether modified silicone. It should be noted that the durable hydrophilic property may also be provided by applying the alkyl phosphate metal salt (which has been mentioned above as one example of the initial hydrophilic agent) in a larger basis weight than in the case where it is employed as the initial hydrophilic agent. In this case, a linear alkyl phosphate potassium salt containing 12 to 22 carbon atoms is preferably employed so as to provide the durable hydrophilic property. Hydrophilicity is set higher in the bottom layer 23b than in the top layer 23a, and the hydrophilicity of the topsheet 24 is set equal to or higher than that of the bottom layer 23b. That is, the top layer 23a of the intermediate sheet 23<the bottom layer 23b of the intermediate sheet 23 the topsheet 24, with respect to the hydrophilicity. Accordingly, the liquid absorbed by the topsheet 24 is attracted by the hydrophilicity of the bottom layer 23b which is positioned beneath the topsheet 24 with the top layer 23a therebetween. Therefore, the liquid is attracted to the bottom layer 23b while being diffused, and then permeates the liquid absorbent layer 22 from the bottom layer 23b of such high hydrophilicity.

Here, the difference between the initial hydrophilic agent and the durable hydrophilic agent is such that, when fibers are wetted with a liquid, the initial hydrophilic agent will be washed off the fiber surface in a short period of time, but the durable hydrophilic agent will remain adhered to the fiber surface for a long time, as compared with the initial hydrophilic agent. On the other hand, the hydrophilicity means power of fiber to attract water, so that power to absorb a liquid can be higher in a fibrous layer having higher hydrophilicity than in a fibrous layer having lower hydrophilicity.

As mentioned above, the initial hydrophilic agents applied to the fibers forming the topsheet 24 and the top layer 23a of the intermediate sheet 23 will gradually drop off from the fibers when given a liquid, but once the fibers are wetted with the liquid, passages for permeation of the liquid through the fibrous sheet can be kept. On the other hand, the bottom layer 23b can keep high hydrophilicity for a long time due to the durable hydrophilic agent.

In the case where the durable hydrophilic agent is used for the bottom layer 23b of the intermediate sheet 23 and the hydrophilicity of the bottom layer 23b is set higher than that of the top layer 23a, moreover, a liquid can be diffused and absorbed even if the fiber density of the top layer 23a is set higher than that of the bottom layer 23b in the intermediate sheet 23. In this case, a liquid given to the intermediate sheet 23 is mainly diffused to surroundings in the top layer 23a, but since the hydrophilicity of the bottom layer 23b is relatively high, the liquid, which is being diffused in the top layer 23a, is attracted to the bottom layer 23b, and then attracted to and absorbed by the absorbent layer 22. Since the fibers forming the bottom layer 23b are coated with the durable hydrophilic agent, moreover, the above-mentioned function can be maintained and performed for a long time, even if a liquid is repeatedly supplied thereto.

It should be noted that the weight ratio of the fibers forming the bottom layer 23b and coated with the durable hydrophilic agent to the intermediate sheet 23 is preferably higher than the weight ratio of the fibers forming the top layer 23a and coated with the initial hydrophilic agent to the intermediate sheet 23, and a difference therebetween is preferably equal to or more than 5% by weight. By making the weight ratio higher in the bottom layer 23b, the function to attract a liquid given to the topsheet 24 to the bottom layer 23b can be improved.

For the liquid absorbent layer 22, any absorbent materials known in the art can be employed, as exemplified by airlaid pulp, a plurality of stacked sheets of tissue paper, or the like. However, in order not to deteriorate a feel during long-time wear, it is preferred that the liquid absorbent layer 22 does not contain particulated superabsorbent polymers (SAPs). If the particulated SAPs are used for thin absorbent articles, the hardness of the particulated SAPs may possibly irritate the skin of a wearer to deteriorate a feel during wear. In case where the liquid absorbent layer 22 is formed of airlaid pulp of which pulp fibers are joined with an acrylic binder, for instance, it feels comfortable to wear and its liquid absorption and retention capacity can be increased. In the case of the airlaid pulp, the basis weight is about 45 g/m$^2$ and the density is about 0.01 g/cm$^3$. In addition, it is of a thin type having a thickness of about 0.3 to 0.7 mm.

The individual adhesive layers 28, 27 and 26 are applied in a plurality of strips having a width of about 0.5 to 1.5 mm, which are arranged at a pitch of 0.5 to 1.5 mm in the transverse direction, as well. Each strip of the adhesive layers preferably has a basis weight of about 7 to 13 g/m$^2$. It should be noted that although the adhesive layers 28, 27 and 26 are depicted to have a given thickness in the sectional view of FIG. 4 and as a result, the topsheet 24, intermediate sheet 23 and liquid absorbent layer 22 are depicted to have clearances therebetween, the adhesive layers are very thin in actual products so that the intermediate sheet 23 is substantially in contact with the topsheet 24 and the liquid absorbent layer 22.

For the adhesive layers 28, 27 and 26 for bonding adjacent sheets of the main body portion 20, preferably used is a hot-melt type olefin adhesive. The hot-melt type olefin adhesive is suitable for a case where the absorbing sheet 10 contains an aroma chemical, especially a citrus aroma chemical. The aroma chemical may be disposed in any gap between adjacent sheets of the main body portion 20. For instance, the aroma chemical may be applied onto the garment surface of the liquid absorbent layer 22 into a strip shape extending in the longitudinal direction and having a width of about 30 to 45 mm. In this case, if the above-mentioned hot-melt type olefin adhesive is used, plasticization of a hot-melt due to volatile components such as limonene contained in the citrus aroma chemical to result in decreasing adhesive force can be prevented.

On the other hand, the backsheet 21 is formed of a PE film having a basis weight of about 23 g/m² and a thickness of tens of μm.

On the exterior surface of the main body portion 20, i.e., on the garment surface of the backsheet 21, there is provided a pressure sensitive adhesive layer 41. This pressure sensitive adhesive layer 41 is applied in a plurality of strips extending in the longitudinal direction and spaced apart from each other by a given distance in the transverse direction. The pressure sensitive adhesive layer 41 is a hot-melt type rubber adhesive. The garment surface of the pressure sensitive adhesive layer 41 is covered with a release sheet 42.

The absorbing sheet 10 is folded at fold lines La and Lb shown in FIG. 1 into a three-ply state shown in FIG. 3, and then wrapped in a packaging film in such folded state. Here, the fold lines La and Lb are preferably set at positions crossing a plurality of liquid passage holes 31. When unfolded from the state shown in FIG. 3 to the state shown in FIG. 1, transversely extending creases are left at the fold lines La and Lb. Since the fiber densities of the individual sheets are increased at the creases, a discharged liquid, when worn, may possibly diffuse transversely along the creases resulting from folding at the fold lines La and Lb. However, in the case where the creases cross the liquid passage holes 31 elongated in the longitudinal direction, the liquid trying to diffuse transversely along the creases can be readily absorbed into the absorbing sheet 10 through the liquid passage holes 31.

For wear, the release sheet 42 on the exterior surface of the main body portion 20 is peeled off after the absorbing sheet 10 is unfolded to the state shown in FIG. 1, and the absorbing sheet 10 is adhered and fixed on an inner side of a crotch portion of an undergarment through the pressure sensitive adhesive layer 41.

A discharged liquid such as vaginal discharge is locally given to the central region 30. The discharged liquid locally given to the central region 30 passes through the topsheet 24 due to capillary action of the liquid passage holes 31, while being diffused in the longitudinal direction along the central region 30 having the liquid passage holes 31 formed therein, and is then given to the liquid absorbent layer 22 from the intermediate sheet 23.

Since the fiber density of the intermediate sheet 23 is higher than that of the topsheet 24, the liquid having passed through the liquid passage holes 31 is diffused in the intermediate sheet 23. Then, the liquid diffused in the intermediate sheet 23 is attracted to the bottom layer 23b through the function of the durable hydrophilic agent having high hydrophilicity, and thereafter, permeates the liquid absorbent layer 22. Accordingly, even though it is of a thin type, its liquid absorption capacity is relatively large.

EXAMPLE

Example

An absorbent article having the same structure as that shown in FIGS. 1 to 5 was prepared.

The topsheet 24 was formed of a through-air bonded nonwoven fabric comprising sheath/core type bicomponent synthetic fibers (the core was PET; the sheath was PE) having a fineness of 2.2 dtex and a fiber length of 44 mm. The basis weight was 25 g/m² and the density was 0.0625 g/cm³.

The intermediate sheet 23 was formed of a through-air bonded nonwoven fabric of which: the top layer 23a was comprised of sheath/core type bicomponent synthetic fibers (the core was PP; the sheath was PE) having a fineness of 3.3 dtex and a fiber length of 44 mm; and the bottom layer 23b was comprised of sheath/core type bicomponent synthetic fibers (the core was PET; the sheath was PE) having a fineness of 2.2 dtex and a fiber length of 51 mm. The basis weight was 25 g/m² (the top layer 23a was 11 g/m²; the bottom layer 23b was 14 g/m²) and the density was 0.0833 g/cm³.

The liquid absorbent layer 22 was formed of airlaid pulp having a basis weight of 45 g m², of which pulp fibers were joined with an acrylic binder. The width W5 of the central region 30 was set at 23 mm, the pitches Py and Px of the liquid passage holes 31 were set at 4 mm and 4 mm, and the longitudinal dimension Hy and the transverse dimension Hx of the liquid passage holes 31 were set at 1.8 mm and 1.0 mm, respectively. Moreover, the thickness of the absorbing sheet 10 was set at 1.05 mm.

Comparative Example

An absorbent article having the same structure as that shown in FIG. 6 was prepared. For the topsheet 4, used was a spunlaced nonwoven fabric comprising 55% by weight of rayon, 30% by weight of PET, and 15% by weight of PP, and having a basis weight of 38 g/m². For the intermediate sheet 3, a fibrous layer formed of a bundle of hydrophobic PP fibers and having a basis weight of 18 g/m² was used as a top layer, and a through-air bonded nonwoven fabric having a basis weight of 30 g/m² was used as a bottom layer.

Evaluation

At a central region of the absorbent articles of Example and Comparative Example, 1 ml of artificial body fluid was dropped onto the body surface of the topsheet at a rate of 1 ml (milliliter)/second. The time required for the artificial body fluid to disappear from the body surface of the topsheet was measured after dropping the artificial body fluid. It took 8 seconds for the absorbent article of Example, and it took 25 seconds for the absorbent article of Comparative Example.

Here, the artificial body fluid was prepared such that 8 g of carboxymethyl cellulose sodium, 80 g of glycerin, 10 g of sodium chloride, 4 g of sodium hydrogen carbonate were added to 1 liter of ion-exchanged water, and 8 g of Red No.102 as a coloring agent was further added thereto.

As has been described hereinabove, even if it is of a thin type, the absorbent article of the present invention can absorb a locally given liquid in a short period of time.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article elongated to have longitudinally opposed front and rear edges and transversely opposed left and right edges, the absorbent article comprising a stack of:
   a backsheet having a liquid barrier effect;
   a liquid absorbent layer;

a hydrophilic intermediate sheet including fibers; and a hydrophilic topsheet formed of a single sheet, wherein the absorbent article has a central region of a predetermined width, which is spaced apart from the left and right edges, the spaces between the central region and the left and right edges respectively defining left and right side regions outside of the central region;

wherein each of the backsheet, liquid absorbent layer, intermediate sheet and topsheet extend across an entire width of the absorbent article, wherein a plurality of liquid passage holes are formed only in the central region and continuously extend from the opposed front and rear edges in a longitudinal direction of the absorbent article, each of the liquid passage holes continuously extend through the topsheet and the intermediate sheet, each of the liquid passage holes being aligned along a common axis through the topsheet and the intermediate sheet, and wherein each liquid passage hole is elongated longitudinally of the absorbent article to have a longitudinal dimension larger than a transverse dimension, and the longitudinal dimension of each liquid passage hole is gradually decreased as extending from a body surface of the topsheet to the intermediate sheet, wherein the topsheet and the intermediate sheet are bonded through a first adhesive layer which is applied in each of left and right side regions as a plurality of strips extending longitudinally and spaced apart from each other transversely, wherein the first adhesive layer for bonding the topsheet and the intermediate sheet is provided exclusively in the left and right side regions transversely outside the central region and having no liquid passage holes, and wherein the thickness of the absorbent article is no greater than 3 mm.

2. The absorbent article as set forth in claim 1, wherein the central region extends longitudinally of the absorbent article in a strip shape of a predetermined width and the liquid passage holes are uniformly distributed in the central region.

3. The absorbent article as set forth in claim 1, wherein a fiber density of the intermediate sheet is higher than a fiber density of the topsheet in the central region.

4. The absorbent article as set forth in claim 3, wherein a difference in fiber density between the topsheet and the intermediate sheet in the central region is equal to or higher than 0.01 g/cm$^3$.

5. The absorbent article as set forth in claim 1, wherein at least one of the topsheet and the intermediate sheet is formed of through-air bonded nonwoven fabric, of which synthetic fibers are thermal bonded to each other with hot air.

6. The absorbent article as set forth in claim 1, wherein fibers forming the topsheet are coated with an initial hydrophilic agent and fibers forming the intermediate sheet are coated with a durable hydrophilic agent.

7. The absorbent article as set forth in claim 6, wherein the intermediate sheet includes a bottom layer adjacent to the liquid absorbent layer and a top layer adjacent to the topsheet, and fibers forming the bottom layer are coated with the durable hydrophilic agent and fibers forming the top layer are coated with the initial hydrophilic agent.

8. The absorbent article as set forth in claim 7, wherein hydrophilicity of the bottom layer of the intermediate sheet is higher than hydrophilicity of the top layer of the intermediate sheet, and hydrophilicity of the topsheet is equal to or higher than the hydrophilicity of the bottom layer of the intermediate sheet.

9. The absorbent article as set forth in claim 1, which has an entire length equal to or larger than 160 mm.

10. The absorbent article as set forth in claim 1, which is adapted for use as a vaginal discharge absorbing sheet.

11. The absorbent article as set forth in claim 1, wherein the intermediate sheet and the liquid absorbent layer are bonded through a second adhesive layer which is applied in a plurality of strips extending longitudinally and spaced apart from each other transversely, the plurality of strips extending substantially over the entire width of the absorbent article.

12. The absorbent article as set forth in claim 1, wherein the liquid absorbent layer and the backsheet are bonded through a third adhesive layer which is applied in a plurality of strips extending longitudinally and spaced apart from each other transversely, the plurality of strips extending substantially over the entire width of the absorbent article.

13. The absorbent article as set forth in claim 1, wherein at least one peripheral edge of the absorbent article has a type of seal that is different from the first adhesive layer provided in the left and right side regions.

\* \* \* \* \*